United States Patent
Petersen

(10) Patent No.: US 10,605,713 B2
(45) Date of Patent: Mar. 31, 2020

(54) DROPLET DEFLECTORS AND METHODS FOR USING THE SAME

(71) Applicant: Becton, Dickinson and Company, Franklin Lakes, NJ (US)

(72) Inventor: Timothy Wayne Petersen, Seattle, WA (US)

(73) Assignee: BECTON, DICKINSON AND COMPANY, Franklin Lakes, NJ (US)

(*) Notice: Subject to any disclaimer, the term of this patent is extended or adjusted under 35 U.S.C. 154(b) by 233 days.

(21) Appl. No.: 15/623,058

(22) Filed: Jun. 14, 2017

(65) Prior Publication Data
US 2018/0095022 A1    Apr. 5, 2018

Related U.S. Application Data

(60) Provisional application No. 62/404,679, filed on Oct. 5, 2016.

(51) Int. Cl.
| | | |
|---|---|---|
| *G01N 15/14* | (2006.01) | |
| *G01N 21/31* | (2006.01) | |
| *B01L 3/02* | (2006.01) | |

(52) U.S. Cl.
CPC .......... *G01N 15/14* (2013.01); *B01L 3/0241* (2013.01); *G01N 15/1459* (2013.01); *G01N 21/31* (2013.01); *B01L 2200/0652* (2013.01); *B01L 2400/0415* (2013.01); *G01N 2015/149* (2013.01); *G01N 2015/1481* (2013.01)

(58) Field of Classification Search
None
See application file for complete search history.

(56) References Cited

U.S. PATENT DOCUMENTS

| 3,963,606 | A | * | 6/1976 | Hogg .................. B07C 5/36 209/3 |
| 6,079,836 | A | | 6/2000 | Burr et al. |
| 8,992,853 | B2 | | 3/2015 | Stratman et al. |
| 2009/0107893 | A1 | * | 4/2009 | Schembri .......... G01N 15/1459 209/127.1 |
| 2012/0080544 | A1 | * | 4/2012 | Shinoda .............. B01F 5/0256 239/690 |

FOREIGN PATENT DOCUMENTS

| EP | 2053380 A2 | 4/2009 |
| WO | WO 2016/089521 A1 | 6/2016 |

OTHER PUBLICATIONS

Durr et al. "Microdevices for manipulation and accumulation of micro- and nanoparticles by dielectrophoresis," Electrophoresis, 2003, vol. 24, No. 4, pp. 722-731.

(Continued)

*Primary Examiner* — Kathryn Wright
(74) *Attorney, Agent, or Firm* — Bret E. Field; Bozicevic, Field & Francis LLP

(57) ABSTRACT

Aspects of the present disclosure include a droplet deflector configured to apply a deflection force to a flow stream at a plurality of different angles. Droplet deflectors according to certain embodiments include one or more sets of parallel metallic plates that are configured to apply a deflection force to droplets in a flow stream flowing therebetween. Systems and methods for sorting particles in a sample with the subject deflector plates are also provided.

21 Claims, 2 Drawing Sheets

(56) References Cited

OTHER PUBLICATIONS

Stanley, Martha: "FACS & Cell Sorting: Cell Isolation," Dec. 21, 2015, Internal Slide pp. 1-24, retrieved from the Internet, URL: http://slideplayer.com/slide/9030540/.
Wang et al. "Dielectrophoresis switching with vertical sidewall electrodes for microfluidic flow cytometry," Lab on a Chip, 2007, vol. 7, No. 9, pp. 1114-1120.

* cited by examiner

DROPLET DEFLECTORS AND METHODS FOR USING THE SAME

CROSS-REFERENCE TO RELATED APPLICATION

Pursuant to 35 U.S.C. § 119(e), this application claims priority to the filing date of U.S. Provisional Patent Application Ser. No. 62/404,679, filed Oct. 5, 2016; the disclosure of which application is incorporated herein by reference.

INTRODUCTION

Flow-type particle sorting systems, such as sorting flow cytometers, are used to sort particles in a fluid sample based on at least one measured characteristic of the particles. In a flow-type particle sorting system, particles, such as molecules, analyte-bound beads, or individual cells, in a fluid suspension are passed in a stream by a detection region in which a sensor detects particles contained in the stream of the type to be sorted. The sensor, upon detecting a particle of the type to be sorted, triggers a sorting mechanism that selectively isolates the particle of interest.

Particle sensing typically is carried out by passing the fluid stream by a detection region in which the particles are exposed to irradiating light, from one or more lasers, and the light scattering and fluorescence properties of the particles are measured. Particles or components thereof can be labeled with fluorescent dyes to facilitate detection, and a multiplicity of different particles or components may be simultaneously detected by using spectrally distinct fluorescent dyes to label the different particles or components. Detection is carried out using one or more photosensors to facilitate the independent measurement of the fluorescence of each distinct fluorescent dye.

To sort particles in the sample, a drop charging mechanism charges droplets of the flow stream containing a particle type to be sorted with an electrical charge at the break-off point of the flow stream. Droplets are passed through an electrostatic field and are deflected based on polarity and magnitude of charge on the droplet into distinct collection containers. Uncharged droplets are not deflected by the electrostatic field and are collected by a receptacle along the longitudinal axis of the flow stream.

SUMMARY

Aspects of the present disclosure include a droplet deflector configured to apply a deflection force to a flow stream at a plurality of different angles. Droplet deflectors according to certain embodiments include two or more parallel metallic plates that are configured to deflect droplets at a plurality of different angles in a flow stream flowing therebetween. The subject droplet deflectors are configured apply a deflection force sufficient to deflect a flow stream droplet by 3 mm or more at a plurality of different angles. In embodiments, the parallel metallic plates are spaced apart by 3 mm or more. In some embodiments, the droplet deflector includes a first set of parallel metallic plates and a second set of parallel metallic plates where the second set of parallel metallic plates is positioned downstream along the flow stream from the first set of parallel metallic plates. In some instances, the second set of metallic plates are positioned at an angle with respect to the first set of metallic plates, such as at an angle that ranges from 1° to 90°. In certain instances, the second set of metallic plates are orthogonal to the first set of metallic plates. In some examples, the first set of metallic plates have a width that is less than the width of the second set of metallic plates. In other examples, the first set of metallic plates have a length that is less than the length of the second set of metallic plates. In yet other examples, the first set of metallic plates have a width that is greater than the second set of metallic plates. In still other examples, the first set of metallic plates have a length that is greater than the second set of metallic plates. In certain embodiments, the droplet deflector includes two parallel twisted metallic plates. In some instances, the droplet deflector is configured to apply a constant deflection force along the length of the twisted metallic plates. In certain instances, the twisted metallic plates have a twist angle of from 1° to 45°.

Aspects of the present disclosure also include particle sorting modules for sorting particle components of a sample, such as cells in a biological sample. Particle sorting modules according to certain embodiments include a flow cell nozzle having a nozzle orifice configured to flow a flow stream through the flow cell nozzle and one or more of the subject droplet deflectors for sorting droplets of the flow stream flowing therebetween by applying a deflection force at a plurality of different angles. In some embodiments, the particle sorting module includes a sample interrogation region in fluid communication with the flow cell nozzle, such as a sample interrogation region having a cuvette. The flow cell nozzle may also be in fluid communication with a sample inlet and a sheath fluid inlet. To sort different droplets of the flow stream, particle sorting modules of interest may also include two or more sample collection containers.

Aspects of the present disclosure also include systems for sorting particle components of a sample. Systems according to certain embodiments include a light source, a flow cell nozzle having a nozzle orifice configured to flow a flow stream through the flow cell nozzle, a detector for measuring one or more wavelengths of light and one or more of the subject droplet deflectors for sorting droplets of the flow stream flowing therebetween by applying a deflection force at a plurality of different angles.

Methods for sorting particles of a sample are also provided. Methods according to certain embodiments include irradiating with a light source a sample having particles in a flow stream, detecting one or more wavelengths of light and sorting particles in the sample into two or more sample collection chambers with a droplet deflector configured to apply a deflection force at a plurality of different angles to the flow stream flowing therebetween. In certain embodiments, the sample is a biological sample and methods include sorting and collecting two or more different types of cells.

BRIEF DESCRIPTION OF THE FIGURES

The invention may be best understood from the following detailed description when read in conjunction with the accompanying drawings. Included in the drawings are the following figures.

DETAILED DESCRIPTION

Figure 1:
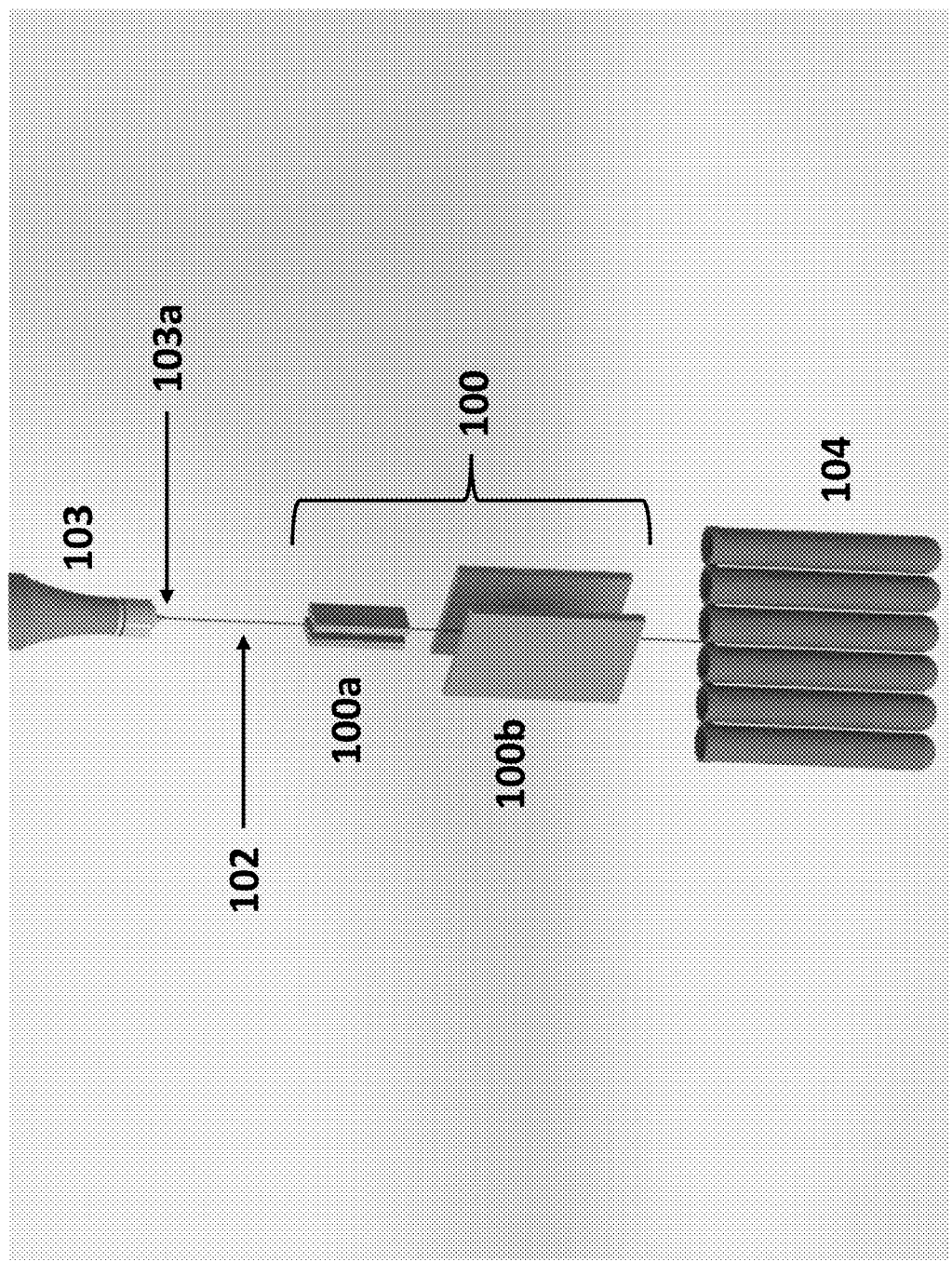
FIG. 1 depicts a droplet deflector having two sets of parallel metallic plates according to certain embodiments.

Aspects of the present disclosure include a droplet deflector configured to apply a deflection force to a flow stream at a plurality of different angles. Droplet deflectors according to certain embodiments include one or more sets of parallel metallic plates that are configured to apply a deflection force to droplets in a flow stream flowing therebetween. Systems and methods for sorting particles in a sample with the subject deflector plates are also provided.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present disclosure provides a droplet deflector configured to apply a deflection force to a flow stream at plurality of different angles. In further describing embodiments of the disclosure, droplet deflectors configured for applying a deflection force to droplets in a flow stream at a plurality of different angles are first described in greater detail. Next, particle sorting modules and systems for separating particles in a sample are described. Methods for sorting droplets in a flow stream are also provided.

Droplet Deflectors for Applying a Deflection Force to a Flow Stream at a Plurality of Different Angles As summarized above, aspects of the present disclosure include droplet deflectors configured to apply a deflection force to a flow stream at a plurality of different angles. The term "deflect" is used herein in its conventional sense to refer to applying a force which diverts droplets in a flow stream from flowing along its normal trajectory (i.e., in the absence of the deflection force) to a different trajectory along the longitudinal axis of the flow stream. Droplets in the flow stream according to embodiments of the present disclosure may be diverted from their normal trajectory along the longitudinal axis of the flow stream by a distance by 0.001 mm or more as measured radially across a plane orthogonal to the longitudinal axis of the flow stream, such as 0.005 mm or more, such as 0.01 mm or more, such as 0.05 mm or more, such as 0.1 mm or more, such as 0.5 mm or more, such as 1 mm or more, such as 2 mm or more, such as 5 mm or more, such as 10 mm or more, such as 15 mm or more, such as 20 mm or more, such as 25 mm or more, such as 30 mm or more, such as 35 mm or more and including 50 mm or more. For example, the droplets in the flow stream may be diverted by a distance of from 0.001 mm to 100 mm, such as from 0.005 mm to 95 mm, such as from 0.001 mm to 90 mm, such as from 0.05 mm to 85 mm, such as from 0.01 mm to 80 mm, such as from 0.05 mm to 75 mm, such as from 0.1 mm to 70 mm, such as from 0.5 mm to 65 mm, such as from 1 mm 60 mm, such as from 5 mm to 55 mm and including from 10 mm to 50 mm. As such, droplets in the flow stream may be deflected by the force of deflection from the longitudinal axis of the flow stream by an angle that ranges from 0.01° to 90°, such as from 0.05° to 85°, such as from 0.1° to 80°, such as from 0.5° to 75°, such as from 10° to 70°, such as from 15° to 65°, such as from 20° to 60°, such as from 25° to 55° and including from 30° to 50°.

As discussed in greater detail below, the subject droplet deflectors may be configured for sorting particles in a sample, such as cells in a biological sample. In these embodiments, the droplet deflector is configured to apply a deflection force sufficient to deflect particles flowing in a flow stream into one or more sample collection containers. Accordingly, the droplet deflectors may be configured to apply a deflection force such that particles in the flow stream are deflected into sample collection containers that are 0.001 mm or more from the longitudinal axis of the flow stream, such as by 0.005 mm or more, such as 0.01 mm or more, such as 0.05 mm or more, such as 0.1 mm or more, such as 0.5 mm or more, such as 1 mm or more, such as 2 mm or more, such as 5 mm or more, such as 10 mm or more, such as 15 mm or more, such as 20 mm or more, such as 25 mm or more, such as 30 mm or more, such as 35 mm or more and including 50 mm or more. For example, droplet deflectors may be configured to deflect particles in the flow stream into sample collection containers that are diverted from the longitudinal axis of the flow stream by a distance of from 0.001 mm to 100 mm, such as from 0.005 mm to 95 mm, such as from 0.001 mm to 90 mm, such as from 0.05 mm to 85 mm, such as from 0.01 mm to 80 mm, such as from 0.05 mm to 75 mm, such as from 0.1 mm to 70 mm, such as from 0.5 mm to 65 mm, such as from 1 mm 60 mm, such as from 5 mm to 55 mm and including from 10 mm to 50 mm.

Droplet deflectors according to embodiments are configured to deflect droplets in a flow stream at a plurality of different angles, such as at 2 different angles or more, such as 3 different angles or more, such as 4 different angles or more, such as at 5 different angles or more, such as 6 different angles or more, such as 7 different angles or more, such as 8 different angles or more, such as 9 different angles or more and including 10 different angles or more. Each angle of deflection may vary depending on the structural configuration of the subject droplet deflector, as described in greater detail below, and may range from 0.01° to 90°, such as from 0.05° to 85°, such as from 0.1° to 80°, such as from 0.5° to 75°, such as from 10° to 70°, such as from 15° to 65°, such as from 20° to 60°, such as from 25° to 55° and including from 30° to 50°.

In embodiments of the present disclosure, the droplet deflector includes two or more metallic plates, such as two or more parallel metallic plates configured to produce an electric field therebetween. The voltage applied to deflector plates to divert charged particles may be 10 mV or more, such as 25 mV or more, such as 50 mV or more, such as 100 mV or more, such as 250 mV or more, such as 500 mV or more, such as 750 mV or more, such as 1000 mV or more, such as 2500 mV or more, such as 5000 mV or more, such as 10000 V or more, such as 15000 V or more, such as 25000 V or more, such as 50000 V or more and including 100000 V or more. In certain embodiments, the voltage applied to each set of parallel metallic plates is from 0.5 kV to 15 kV, such as from 1 kV to 15 kV, such as from 1.5 kV to 12.5 kV and including from 2 kV to 10 kV. In certain embodiments, the voltage applied to each set of parallel metallic plates is from 0.5 kV to 15 kV, such as from 1 kV to 15 kV, such as from 1.5 kV to 12.5 kV and including from 2 kV to 10 kV. Depending on the voltage applied to the metallic plates, the electric field strength between the metallic plates may vary, ranging from 0.001 V/m to $1 \times 10^7$ V/m, such as from 0.01 V/m to $5 \times 10^6$ V/m, such as from 0.1 V/m to $1 \times 10^6$ V/m, such as from 0.5 V/m to $5 \times 10^5$, such as from 1 V/m to $1 \times 10^5$ V/m, such as from 5 V/m to $5 \times 10^4$ V/m, such as from 10 V/m to $1 \times 10^4$ V/m and including from 50 V/m to $5 \times 10^3$ V/m, for example $1 \times 10^5$ V/m to $2 \times 10^6$ V/m.

The subject parallel metallic plates include two metallic plates which are spaced apart from each other by a distance sufficient to generate an electric field therebetween. For example, the parallel metallic plates may be spaced apart by 0.01 mm or more, such as 0.05 mm or more, such as 0.1 mm or more, such as 0.5 mm or more, such, as 1 mm or more, such as 1.5 mm or more, such as 2 mm or more, such as 2.5 mm or more, such as 3 mm or more, such as 3.5 mm or more, such as 4 mm or more, such as 4.5 mm or more, such as 5 mm or more, such as 10 mm or more, such as 15 mm or more, such as 20 mm or more and including 25 mm or more. In some instances, the parallel metallic plates are spaced apart by a distance that ranges from 0.01 mm to 50 mm, such as from 0.05 mm to 45 mm, such as from 0.1 mm to 40 mm, such as from 0.5 mm to 35 mm, such as from 1 mm to 30 mm, such as from 1.5 mm to 25 mm, such as from 2 mm to 20 mm and including from 3 mm to 15 mm.

The subject droplet deflectors may include 2 or more sets of parallel metallic plates, such as 3 or more, such as 4 or more, such as 5 or more, such as 6 or more, such as 7 or more, such as 8 or more, such as 9 or more and including 10 or more sets of parallel metallic plates. As described in greater detail below, in some embodiments a deflection force is applied to droplets in the flow stream by applying a voltage to the parallel metallic plates resulting in an electric field that accelerates and diverts the trajectory of target droplets from the longitudinal axis of the flow stream to one or more sample collection containers. The voltage applied to each set of parallel metallic plates may be the same or different. Where the voltage applied to each set of parallel metallic plates is different, the difference between the applied voltage may be 0.01 mV or more, such as 0.05 mV or more, such as 0.1 mV or more, such as 0.5 mV or more, such as 1 mV or more, such as 5 mV or more, such as 10 mV or more, such as 25 mV or more, such as 50 mV or more, such as 75 mV or more, such as 100 mV or more, such as 250 mV or more, such as 500 mV or more, such as 750 mV or more, such as 1 V or more, such as 2.5 V or more, such as 5 V or more, such as 10 V or more, such as 25 V or more, such as 50 V or more and including 100 V or more, such as 500 V or more, such as 1000 V or more. In certain embodiments, the difference between the applied voltage may range from 0.5 kV to 15 kV, such as from 1 kV to 15 kV, such as from 1.5 kV to 12.5 kV and including from 2 kV to 10 kV.

Depending on the applied voltage, the electric field strength between each set of parallel metallic plates may be the same or different. In certain embodiments, the electric field strength between each set of parallel metallic plates is the same and droplets flowing in the flow stream are subjected to a constant electric field through the droplet deflector. In other embodiments, the electric field strength between each set of parallel metallic plate is different and the electric field strength differs by 0.001 V/m or more, such as by 0.01 V/m or more, such as by 0.1 V/m or more, such as by 0.5 V/m or more, such as by 1 V/m or more, such as by 2 V/m or more, such as by 5 V/m or more, such as by 10 V/m or more and including by 25 V/m or more, such as by 50 V/m or more, such as by 100 V/m or more, such as by 500 V/m or more and including by $1 \times 10^3$ V/m or more.

The parallel metallic plates of the subject droplet deflectors may be formed from any suitable metal capable of producing an electric field and may include but is not limited to aluminum, brass, chromium, cobalt, copper, gold, indium, iron, lead, nickel, platinum, palladium, tin, steel (e.g., stainless steel), silver, zinc and combinations and alloys thereof, such as for example an aluminum alloy, aluminum-lithium alloy, an aluminum-nickel-copper alloy, an aluminum-copper alloy, an aluminum-magnesium alloy, an aluminum-magnesium oxide alloy, an aluminum-silicon alloy, an aluminum-magnesium-manganese-platinum alloy, a cobalt alloy, a cobalt-chromium alloy, a cobalt-tungsten alloy, a cobalt-molybdenum-carbon alloy, a cobalt-chromium-nickel-molybdenum-iron-tungsten alloy, a copper alloy, a copper-arsenic alloy, a copper-berrylium alloy, a copper-silver alloy, a copper-zinc alloy (e.g., brass), a copper-tin alloy (e.g., bronze), a copper-nickel alloy, a copper-tungsten alloy, a copper-gold-silver alloy, a copper-nickel-iron alloy, a copper-manganese-tin alloy, a copper-aluminum-zinc-tin alloy, a copper-gold alloy, a gold alloy, a gold-silver alloy, an indium alloy, an indium-tin alloy, an indium-tin oxide alloy, an iron alloy, an iron-chromium alloy (e.g., steel), an iron-chromium-nickel alloy (e.g., stainless steel), an iron-silicon alloy, an iron-chromium-molybdenum alloy, an iron-carbon alloy, an iron-boron alloy, an iron-magnesium alloy, an iron-manganese alloy, an iron molybdenum alloy, an iron-nickel alloy, an iron-phosphorus alloy, an iron-titanium alloy, an iron-vanadium alloy, a lead alloy, a lead-antimony alloy, a lead-copper alloy, a lead-tin alloy, a lead-tin-antimony alloy, a nickel alloy, a nickel-manganese-aluminum-silicon alloy, a nickel-chromium alloy, a nickel-copper alloy, a nickel, molybdenum-chromium-tungsten alloy, a nickel-copper-iron-manganese alloy, a nickel-carbon alloy, a nickel-chromium-iron alloy, a nickel-silicon alloy, a nickel-titanium alloy, a silver alloy, a silver-copper alloy (e.g., sterling silver) a silver-coper-germanium alloy (e.g., Argentium sterling silver), a silver-gold alloy, a silver-copper-gold alloy, a silver-platinum alloy, a tin alloy, a tin-copper-antimony alloy, a tin-lead-copper alloy, a tin-lead-antimony alloy, a titanium alloy, a titanium-vanadium-chromium alloy, a titanium-aluminum alloy, a titanium-aluminum-vanadium alloy, a zinc alloy, a zinc-copper alloy, a zinc-aluminum-magnesium-copper alloy, a zirconium alloy, a zirconium-tin alloy or a combination thereof.

The parallel metallic plates of the subject droplet deflectors may be any suitable shape, such as a circle, oval, half-circle, crescent-shaped, star-shaped, square, triangle, rhomboid, pentagon, hexagon, heptagon, octagon, rectangle or other suitable polygon. In certain embodiments, the parallel metallic plates are rectangular. As described in greater detail below, in certain instances the parallel metallic plates are twisted, such as twisted rectangles having a twist angle that 5° or more, such as 10° or more, such as 15° or more, such as 20° or more, such as 25° or more, such as 30° or more, such as 35° or more, such as 40° or more, such as 45° or more, such as 50° or more, such as 55° or more and including having a twist angle of 60° or more.

Depending on the shape of the metallic plates, the dimensions may vary. In some embodiments, each metallic plate has a width that ranges from 0.5 mm to 10 mm, such as from 1 mm to 9.5 mm, such as from 1.5 mm to 9 mm, such as from 2 mm to 8.5 mm, such as from 2.5 mm to 8 mm, such as from 3 mm to 7.5 mm, such as from 3.5 mm to 7 mm, such as from 4 mm to 6.5 mm and including a width than ranges from 4.5 mm to 6 mm. The length also varies ranging from 10 mm to 500 mm, such as from 15 mm to 450 mm, such as from 20 mm to 400 mm, such as from 25 mm to 350 mm, such as from 30 mm to 300 mm, such as from 35 mm to 250 mm, such as from 40 mm to 200 mm, such as from 45 mm to 150 mm and including from 50 mm to 100 mm. In certain embodiments, the metallic plates are an asymmetric polygon where a first end has a width that is smaller than the width of the second end. The width at each end may range from 0.01 mm to 10 mm, such as from 0.05 mm to 9.5 mm, such as from 0.1 mm to 9 mm, such as from 0.5 mm to 8.5 mm, such as from 1 mm to 8 mm, such as from 2 mm to 8 mm, such as from 2.5 mm to 7.5 mm and including from 3 mm to 6 mm. In certain embodiments, the cover bar is an asymmetric polygon having a first end having a width from 1 to 10 mm and a second end having a width from 2 to 5 mm. For example, the cover bar may be an asymmetric polygon having a first end having a 5 mm width and a second end having a 10 mm width. In embodiments, the surface area of each metallic plate may vary as desired and may range from 0.25 to 15 cm$^2$, such as 0.5 to 14 cm$^2$, such as 0.75 to 13 cm$^2$, such as 1 to 12 cm$^2$, such as 1.5 to 11 cm$^2$, and including 2 to 10 cm$^2$.

In some embodiments, droplet deflectors of interest include a first set of parallel metallic plates and a second set of parallel metallic plates positioned downstream (along the flow path of the flow stream) from the first set of parallel metallic plates. Depending on the desired angles of deflection, the second set of parallel metallic plates may be positioned at an angle of from 5° to 90° with respect to the first set of parallel metallic plates, such as from 10° to 85°, such as from 15° to 80°, such as from 20° to 75°, such as from 25° to 70°, such as from 30° to 65°, such as from 35° to 60° and including where the second set of parallel metallic plates are positioned at an angle of from 40° to 55° with respect to first set of parallel metallic plates. In one example, the second set of parallel metallic plates are positioned at a 30° angle with respect to the first set of parallel metallic plates. In another example, the second set of parallel metallic plates are positioned at a 45° angle with respect to the first set of parallel metallic plates. In yet another example, the second set of parallel metallic plates are positioned at a 60° angle with respect to the first set of parallel metallic plates. In still another example, second set of parallel metallic plates are orthogonal to the first set of parallel metallic plates.

In these embodiments, the shape and size of the first set of parallel metallic plates may be the same or different from the second set of parallel metallic plates. In some embodiments the shape of the first set of parallel metallic plates is the same as the second set of parallel metallic plates (e.g., both rectangular). In other embodiments, the shape of the first set of parallel metallic plates is different from the second set of parallel metallic plates (e.g., the first set of parallel metallic plates are square and the second set of parallel metallic plates are rectangular). In some instances, the dimensions of the first set of parallel metallic plates are the same as the second set of parallel metallic plates. In one example, the width of the first set of parallel metallic plates is the same as the second set of parallel metallic plates. In other instances, the length of the first set of parallel metallic plates is the same as the second set of parallel metallic plates. In still other instances, the width and length of the first set of parallel metallic plates are the same as the second set of parallel metallic plates. In some examples, the dimensions of the first set of parallel metallic plates are different from the second set of parallel metallic plates. In one example, the width of the first set of parallel metallic plates is different from the second set of parallel metallic plates. In another example, the length of the first set of parallel metallic plates is different from the second set of parallel metallic plates. In yet another example, both the width and the length of the first set of parallel metallic plates is different from the second set of parallel metallic plates.

Where the droplet deflector includes more than one set of parallel metallic plates, each set of parallel metallic plates is configured to divert the trajectory of target droplets by a predetermined distance and angle from the longitudinal axis of the flow stream. In certain embodiments, the droplet deflector includes two sets of parallel metallic plates, the first set of parallel metallic plates are configured to divert the target droplets in the flow stream by a distance that ranges from 0.001 mm to 100 mm, such as from 0.005 mm to 95 mm, such as from 0.001 mm to 90 mm, such as from 0.05 mm to 85 mm, such as from 0.01 mm to 80 mm, such as from 0.05 mm to 75 mm, such as from 0.1 mm to 70 mm, such as from 0.5 mm to 65 mm, such as from 1 mm 60 mm, such as from 5 mm to 55 mm and including from 10 mm to 50 mm and an angle of from 0.01° to 90°, such as from 0.05° to 85°, such as from 0.1° to 80°, such as from 0.5° to 75°, such as from 10° to 70°, such as from 15° to 65°, such as from 20° to 60°, such as from 25° to 55° and including from 30° to 50° and the second set of parallel metallic plates are configured to divert the target droplets in the flow stream by a distance that ranges from 0.001 mm to 100 mm, such as from 0.005 mm to 95 mm, such as from 0.001 mm to 90 mm, such as from 0.05 mm to 85 mm, such as from 0.01 mm to 80 mm, such as from 0.05 mm to 75 mm, such as from 0.1 mm to 70 mm, such as from 0.5 mm to 65 mm, such as from 1 mm 60 mm, such as from 5 mm to 55 mm and including from 10 mm to 50 mm and an angle of from 0.01° to 90°, such as from 0.05° to 85°, such as from 0.1° to 80°, such as from 0.5° to 75°, such as from 10° to 70°, such as from 15° to 65°, such as from 20° to 60°, such as from 25° to 55° and including from 30° to 50°. In this embodiment, the electric field generated between the first set of parallel metallic plates and the second parallel metallic plates may be the same or different, as desired. In one example, the electric field is the same. In another example, the electric field is different, such as where the electric field strength differs by 0.001 V/m or more, such as 0.01 V/m or more, such as 0.1 V/m or more, such as 0.5 V/m or more, such as 1 V/m or more, such as 2 V/m or more, such as 5 V/m or more, such as 10 V/m or more and including 25 V/m or more. In some instances, the electric field between the first set of parallel metallic plates is greater than the electric field between the second set of parallel metallic plates. In other instances, the electric field between the first set of parallel metallic plates is less than the electric field between the second set of parallel metallic plates.

FIG. 1 depicts a droplet deflector having two sets of parallel metallic plates according to certain embodiments. Droplet deflector 100 includes a first set of parallel metallic plates 100a and a second set of parallel metallic plates 100b positioned downstream along the longitudinal axis of flow stream 102 from metallic plates 100a. Flow stream 102 emanates from flow nozzle 103 at nozzle orifice 103a. Metallic plates 100b are oriented orthogonally with respect to metallic plates 100a. Parallel metallic plates 100a are configured to accelerate and deflect droplets in flow stream 102 at a first angle based on the polarity and charge of the droplets. Parallel metallic plates 100b are configured to accelerate and deflect the droplets downstream from parallel metallic plates 100a at a second angle based on the polarity and charge of the droplets. Deflected droplets are collected in sample collection containers 104 downstream from parallel metallic plates 100b.

In certain embodiments, the parallel metallic plates are twisted. In these embodiments, the parallel metallic plates have identical twist angles and remain spaced apart from each other at the same distance along the entire length of the metallic plates. In these embodiments, the applied deflection force also remains constant across the entire length of the twisted metallic plates. Depending on the desired angle of deflection, the twist angle of twisted parallel metallic plates may vary and may be 5° or more, such as 10° or more, such as 15° or more, such as 20° or more, such as 25° or more, such as 30° or more, such as 35° or more, such as 40° or more, such as 45° or more, such as 50° or more, such as 55° or more and including having a twist angle of 60° or more. For example, the twist angle may range from 1° to 90°, such as from 2° to 85°, such as from 3° to 80°, such as from 4° to 75°, such as from 5° to 70°, such as from 10° to 60°, such as from 15° to 45° and including a twist angle from 20° to 40°.

In some embodiments, the twisted parallel metallic plates are twisted by 1 helical twist or less, such as by 0.9 helical twists or less, such as by 0.8 helical twist or less, such as by 0.7 helical twist or less, such as by 0.6 helical twist or less and including by 0.5 helical twist or less. In certain embodiments, the twisted parallel metallic plates have a twist configuration such that the proximal end of the twisted parallel metallic plates are oriented at an angle of from 1° to 90° with respect to the distal end of the twisted parallel metallic plates, such as from 2° to 85°, such as from 3° to 80°, such as from 4° to 75°, such as from 5° to 70°, such as from 10° to 60°, such as from 15° to 45° and including a twist angle from 20° to 40°. In certain embodiments, the proximal end of the twisted parallel metallic plates is orthogonally oriented with respect to the distal end.

Figure 2:
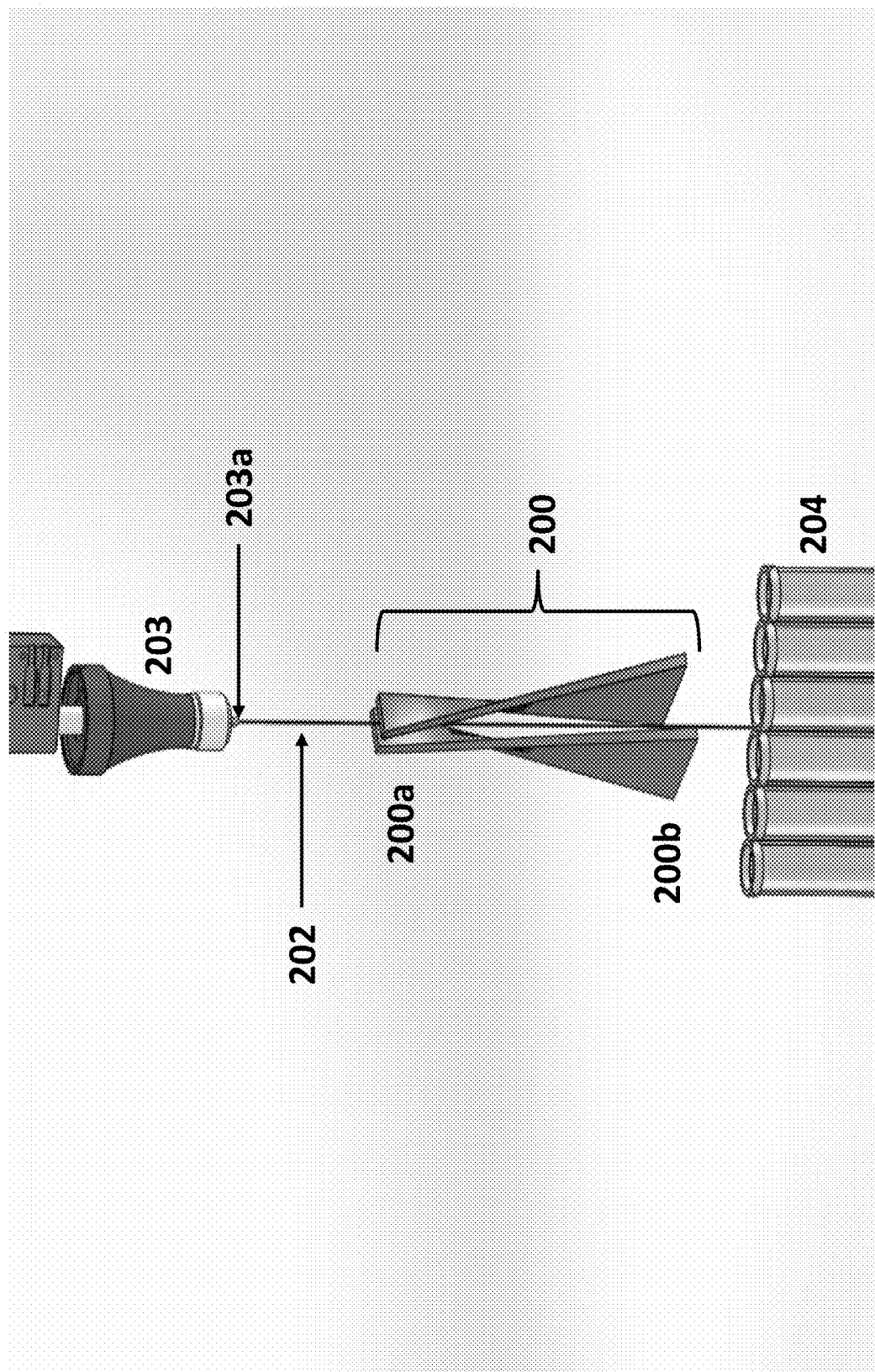
FIG. 2 depicts a droplet deflector having a set of twisted parallel metallic plates according to certain embodiments.

FIG. 2 depicts a droplet deflector having a set of twisted parallel metallic plates according to certain embodiments. Droplet deflector 200 includes a pair of parallel metallic plates having a proximal end 200a and a distal end 200b downstream along the longitudinal axis of flow stream 202 from proximal end 200a. Flow stream 202 emanates from flow nozzle 203 at nozzle orifice 203a. The parallel metallic plates of droplet deflector 200 are twisted such that proximal end 200a is orthogonal with respect to distal end 200b. Twisted parallel metallic plates 200 are configured to accelerate and deflect droplets in flow stream 202 based on the polarity and charge of the droplets. Deflected droplets are collected in sample collection containers 204 downstream from twisted parallel metallic plates 200.

Particle Sorting Modules

Aspects of the present disclosure include a particle sorting module for sorting components of a sample, such as cells in a biological sample. The term "sorting" is used herein in its conventional sense to refer to separating components (e.g., cells, non-cellular particles such as biological macromolecules) of the sample and in some instances, as described below, delivering the separated components to a receiving location having one or more containers. For example, the subject particle sorting modules may be configured for sorting samples having 2 or more components, such as 3 or more components, such as 4 or more components, such as 5 or more components, such as 10 or more component, such as 15 or more components and including soring a sample having 25 or more components. One or more of the sample components may be separated from the sample and delivered to a container, such as 2 or more sample components, such as 3 or more sample components, such as 4 or more sample components, such as 5 or more sample components, such as 10 or more sample components and including 15 or more sample components may be separated from the sample and delivered to a container at the receiving location.

In embodiments, particle sorting modules include one or more of the droplet deflectors described herein that are configured to apply a deflection force at a plurality of different angles and to divert droplets containing analyzed particles to a receiving location. Diversion of a droplet of interest to a receiving location may be achieved by the droplet deflector via electrostatic charging of the droplet and deflection of the charged droplet from the flow stream by the application of an electrostatic field. The voltage applied to the metallic plates of the droplet deflectors in the subject particle sorting modules may be 10 mV or more, such as 25 mV or more, such as 50 mV or more, such as 75 mV or more, such as 100 mV or more, such as 250 mV or more, such as 500 mV or more, such as 750 mV or more, such as 1 V or more, such as 2.5 V or more, such as 5 V or more, such as 10 V or more, such as 25 V or more, such as 50 V or more and including 100 V or more, such as 500 V or more, such as 1000 V or more, such as 5000 V or more, such as 10000 V or more, such as 15000 V or more, such as 25000 V or more, such as 50000 V or more and including 100000 V or more. In certain embodiments, the voltage applied to each set of parallel metallic plates is from 0.5 kV to 15 kV, such as from 1 kV to 15 kV, such as from 1.5 kV to 12.5 kV and including from 2 kV to 10 kV.

The particle sorting module is configured to produce an analyzed stream of droplets and deflect each analyzed droplet from the stream of analyzed droplets to a deflected droplet receiving location. As used herein, the term "deflected droplet receiving location" refers to a location downstream from the droplet deflectors where a sorted droplet containing a cell of interest may be collected after it has been deflected by the droplet deflector plates. As described above, droplets in the flow stream may be diverted from their normal trajectory along the longitudinal axis of the flow stream by a distance by 0.001 mm or more as measured radially across a plane orthogonal to the longitudinal axis of the flow stream, such as 0.005 mm or more, such as 0.01 mm or more, such as 0.05 mm or more, such as 0.1 mm or more, such as 0.5 mm or more, such as 1 mm or more, such as 2 mm or more, such as 5 mm or more, such as 10 mm or more, such as 15 mm or more, such as 20 mm or more, such as 25 mm or more, such as 30 mm or more, such as 35 mm or more and including 50 mm or more. For example, the droplets in the flow stream may be diverted by a distance of from 0.001 mm to 100 mm, such as from 0.005 mm to 95 mm, such as from 0.001 mm to 90 mm, such as from 0.05 mm to 85 mm, such as from 0.01 mm to 80 mm, such as from 0.05 mm to 75 mm, such as from 0.1 mm to 70 mm, such as from 0.5 mm to 65 mm, such as from 1 mm 60 mm, such as from 5 mm to 55 mm and including from 10 mm to 50 mm. As such, the droplet receiving location may be 0.001 mm or more from the longitudinal axis of the flow stream, such as 0.005 mm or more, such as 0.01 mm or more, such as 0.05 mm or more, such as 0.1 mm or more, such as 0.5 mm or more, such as 1 mm or more, such as 2 mm or more, such as 5 mm or more, such as 10 mm or more, such as 15 mm or more, such as 20 mm or more, such as 25 mm or more, such as 30 mm or more, such as 35 mm or more and including 50 mm or more from the longitudinal axis of the flow stream. The droplet receiving location of the subject particle sorting modules may be at a plurality of different angle with respect to the longitudinal axis of the flow stream, such as 0.01° to 90°, such as from 0.05° to 85°, such as from 0.1° to 80°, such as from 0.5° to 75°, such as from 10° to 70°, such as from 15° to 65°, such as from 20° to 60°, such as from 25° to 55° and including from 30° to 50°.

In embodiments, particle sorting modules also include a flow cell nozzle having a nozzle orifice configured to flow a flow stream through the flow cell nozzle and one or more of the subject droplet deflectors described above, which are configured to apply a deflection force at a plurality of different angles to the flow stream flowing therebetween. The subject particle sorting module includes a flow cell nozzle having an orifice which propagates a fluidic sample to a sample interrogation region, where in some embodiments, the flow cell nozzle includes a proximal cylindrical portion defining a longitudinal axis and a distal frustoconical portion which terminates in a flat surface having the nozzle orifice that is transverse to the longitudinal axis. The length of the proximal cylindrical portion (as measured along the longitudinal axis) may vary ranging from 1 mm to 15 mm, such as from 1.5 mm to 12.5 mm, such as from 2 mm to 10 mm, such as from 3 mm to 9 mm and including from 4 mm to 8 mm. The length of the distal frustoconical portion (as measured along the longitudinal axis) may also vary, ranging from 1 mm to 10 mm, such as from 2 mm to 9 mm, such as from 3 mm to 8 mm and including from 4 mm to 7 mm. The diameter of the of the flow cell nozzle chamber may vary, in some embodiments, ranging from 1 mm to 10 mm, such as from 2 mm to 9 mm, such as from 3 mm to 8 mm and including from 4 mm to 7 mm.

In certain instances, the nozzle chamber does not include a cylindrical portion and the entire flow cell nozzle chamber is frustoconically shaped. In these embodiments, the length of the frustoconical nozzle chamber (as measured along the longitudinal axis transverse to the nozzle orifice), may range from 1 mm to 15 mm, such as from 1.5 mm to 12.5 mm, such as from 2 mm to 10 mm, such as from 3 mm to 9 mm and including from 4 mm to 8 mm. The diameter of the proximal portion of the frustoconical nozzle chamber may range from 1 mm to 10 mm, such as from 2 mm to 9 mm, such as from 3 mm to 8 mm and including from 4 mm to 7 mm.

In embodiments, the sample flow stream emanates from an orifice at the distal end of the flow cell nozzle. Depending on the desired characteristics of the flow stream, the flow cell nozzle orifice may be any suitable shape where cross-sectional shapes of interest include, but are not limited to: rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In certain embodiments, flow cell nozzle of interest has a circular orifice. The size of the nozzle orifice may vary, in some embodiments ranging from 1 μm to 20000 μm, such as from 2 μm to 17500 μm, such as from 5 μm to 15000 μm, such as from 10 μm to 12500 μm, such as from 15 μm to 10000 μm, such as from 25 μm to 7500 μm, such as from 50 μm to 5000 μm, such as from 75 μm to 1000 μm, such as from 100 μm to 750 μm and including from 150 μm to 500 μm. In certain embodiments, the nozzle orifice is 100 μm.

In some embodiments, the flow cell nozzle includes a sample injection port configured to provide a sample to the flow cell nozzle. In embodiments, the sample injection system is configured to provide suitable flow of sample to the flow cell nozzle chamber. Depending on the desired characteristics of the flow stream, the rate of sample conveyed to the flow cell nozzle chamber by the sample injection port may be 1 μL/sec or more, such as 2 μL/sec or more, such as 3 μL/sec or more, such as 5 μL/sec or more, such as 10 μL/sec or more, such as 15 μL/sec or more, such as 25 μL/sec or more, such as 50 μL/sec or more, such as 100 μL/sec or more, such as 150 μL/sec or more, such as 200 μL/sec or more, such as 250 μL/sec or more, such as 300 μL/sec or more, such as 350 μL/sec or more, such as 400 μL/sec or more, such as 450 μL/sec or more and including 500 μL/sec or more. For example, the sample flow rate may range from 1 μL/sec to about 500 μL/sec, such as from 2 μL/sec to about 450 μL/sec, such as from 3 μL/sec to about 400 μL/sec, such as from 4 μL/sec to about 350 μL/sec, such as from 5 μL/sec to about 300 μL/sec, such as from 6 μL/sec to about 250 μL/sec, such as from 7 μL/sec to about 200 μL/sec, such as from 8 μL/sec to about 150 μL/sec, such as from 9 μL/sec to about 125 μL/sec and including from 10 μL/sec to about 100 μL/sec.

The sample injection port may be an orifice positioned in a wall of the nozzle chamber or may be a conduit positioned at the proximal end of the nozzle chamber. Where the sample injection port is an orifice positioned in a wall of the nozzle chamber, the sample injection port orifice may be any suitable shape where cross-sectional shapes of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion. In certain embodiments, the sample injection port has a circular orifice. The size of the sample injection port orifice may vary depending on shape, in certain instances, having an opening ranging from 0.1 mm to 5.0 mm, e.g., 0.2 to 3.0 mm, e.g., 0.5 mm to 2.5 mm, such as from 0.75 mm to 2.25 mm, such as from 1 mm to 2 mm and including from 1.25 mm to 1.75 mm, for example 1.5 mm.

In certain instances, the sample injection port is a conduit positioned at a proximal end of the flow cell nozzle chamber. For example, the sample injection port may be a conduit positioned to have the orifice of the sample injection port in line with the flow cell nozzle orifice. Where the sample injection port is a conduit positioned in line with the flow cell nozzle orifice, the cross-sectional shape of the sample injection tube may be any suitable shape where cross-sectional shapes of interest include, but are not limited to: rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. The orifice of the conduit may vary depending on shape, in certain instances, having an opening ranging from 0.1 mm to 5.0 mm, e.g., 0.2 to 3.0 mm, e.g., 0.5 mm to 2.5 mm, such as from 0.75 mm to 2.25 mm, such as from 1 mm to 2 mm and including from 1.25 mm to 1.75 mm, for example 1.5 mm. The shape of the tip of the sample injection port may be the same or different from the cross-section shape of the sample injection tube. For example, the orifice of the sample injection port may include a beveled tip having a bevel angle ranging from 1° to 10°, such as from 2° to 9°, such as from 3° to 8°, such as from 4° to 7° and including a bevel angle of 5°.

In some embodiments, the flow cell nozzle also includes a sheath fluid injection port configured to provide a sheath fluid to the flow cell nozzle. In embodiments, the sheath fluid injection system is configured to provide a flow of sheath fluid to the flow cell nozzle chamber, for example in conjunction with the sample to produce a laminated flow stream of sheath fluid surrounding the sample flow stream. Depending on the desired characteristics of the flow stream, the rate of sheath fluid conveyed to the flow cell nozzle chamber by the may be 25 µL/sec or more, such as 50 µL/sec or more, such as 75 µL/sec or more, such as 100 µL/sec or more, such as 250 µL/sec or more, such as 500 µL/sec or more, such as 750 µL/sec or more, such as 1000 µL/sec or more and including 2500 µL/sec or more. For example, the sheath fluid flow rate may range from 1 µL/sec to about 500 µL/sec, such as from 2 µL/sec to about 450 µL/sec, such as from 3 µL/sec to about 400 µL/sec, such as from 4 µL/sec to about 350 µL/sec, such as from 5 µL/sec to about 300 µL/sec, such as from 6 µL/sec to about 250 µL/sec, such as from 7 µL/sec to about 200 µL/sec, such as from 8 µL/sec to about 150 µL/sec, such as from 9 µL/sec to about 125 µL/sec and including from 10 µL/sec to about 100 µL/sec.

In some embodiments, the sheath fluid injection port is an orifice positioned in a wall of the nozzle chamber. The sheath fluid injection port orifice may be any suitable shape where cross-sectional shapes of interest include, but are not limited to: rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. The size of the sample injection port orifice may vary depending on shape, in certain instances, having an opening ranging from 0.1 mm to 5.0 mm, e.g., 0.2 to 3.0 mm, e.g., 0.5 mm to 2.5 mm, such as from 0.75 mm to 2.25 mm, such as from 1 mm to 2 mm and including from 1.25 mm to 1.75 mm, for example 1.5 mm.

The particle sorting module also includes a sample interrogation region in fluid communication with the flow cell nozzle orifice. As described in greater detail below, a sample flow stream emanates from an orifice at the distal end of the flow cell nozzle and particles in the flow stream may be irradiated with a light source at the sample interrogation region of the particle sorting module. The size of the interrogation region of the particle sorting module may vary depending on the properties of the flow nozzle, such as the size of the nozzle orifice and sample injection port size. In embodiments, the interrogation region may have a width that is 0.01 mm or more, such as 0.05 mm or more, such as 0.1 mm or more, such as 0.5 mm or more, such as 1 mm or more, such as 2 mm or more, such as 3 mm or more, such as 5 mm or more and including 10 mm or more. The length of the interrogation region may also vary, ranging in some instances along 0.01 mm or more, such as 0.1 mm or more, such as 0.5 mm or more, such as 1 mm or more, such as 1.5 mm or more, such as 2 mm or more, such as 3 mm or more, such as 5 mm or more, such as 10 or more, such as 15 mm or more, such as 20 mm or more, such as 25 mm or more and including 50 mm or more of the particle sorting module.

The interrogation region on the particle sorting module may be configured to facilitate irradiation of a planar cross-section of an emanating flow stream or may be configured to facilitate irradiation of a diffuse field (e.g., with a diffuse laser or lamp) of a predetermined length. In some embodiments, the interrogation region on the particle sorting module includes a transparent window that facilitates irradiation of a predetermined length of an emanating flow stream, such as 1 mm or more, such as 2 mm or more, such as 3 mm or more, such as 4 mm or more, such as 5 mm or more and including 10 mm or more. Depending on the light source used to irradiate the emanating flow stream (as described below), the interrogation region of the particle sorting module may be configured to pass light that ranges from 100 nm to 1500 nm, such as from 150 nm to 1400 nm, such as from 200 nm to 1300 nm, such as from 250 nm to 1200 nm, such as from 300 nm to 1100 nm, such as from 350 nm to 1000 nm, such as from 400 nm to 900 nm and including from 500 nm to 800 nm. As such, the particle sorting module at the interrogation region may be formed from any transparent material which passes the desired range of wavelength, including but not limited to optical glass, borosilicate glass, Pyrex glass, ultraviolet quartz, infrared quartz, sapphire as well as plastic, such as polycarbonates, polyvinyl chloride (PVC), polyurethanes, polyethers, polyamides, polyimides, or copolymers of these thermoplastics, such as PETG (glycol-modified polyethylene terephthalate), among other polymeric plastic materials, including polyester, where polyesters of interest may include, but are not limited to poly (alkylene terephthalates) such as poly(ethylene terephthalate) (PET), bottle-grade PET (a copolymer made based on monoethylene glycol, terephthalic acid, and other comonomers such as isophthalic acid, cyclohexene dimethanol, etc.), poly(butylene terephthalate) (PBT), and poly (hexamethylene terephthalate); poly(alkylene adipates) such as poly(ethylene adipate), poly(1,4-butylene adipate), and poly(hexamethylene adipate); poly(alkylene suberates) such as poly(ethylene suberate); poly(alkylene sebacates) such as poly(ethylene sebacate); poly(ε-caprolactone) and poly(β-propiolactone); poly(alkylene isophthalates) such as poly (ethylene isophthalate); poly(alkylene 2,6-naphthalene-dicarboxylates) such as poly(ethylene 2,6-naphthalene-dicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1,4-cyclohexanediylalkylene dicarboxylates) such as poly(trans-1,4-cyclohexanediyl ethylene dicarboxylate); poly(1,4-cyclohexanedimethylene alkylene dicarboxylates) such as poly(1,4-cyclohexane-dimethylene ethylene dicarboxylate); poly ([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as (S)-polylactide, (R,S)-polylactide, poly(tetramethylglycolide), and poly(lactide-co-glycolide); and polycarbonates of bisphenol A, 3,3'-dimethylbisphenol A, 3,3',5,5'-tetrachlorobisphenol A, 3,3',5,5'-tetramethylbisphenol A; polyamides such as poly(p-phenylene terephthalamide); polyesters, e.g., polyethylene terephthalates, e.g., Mylar™ polyethylene terephthalate; etc. In some embodiments, particle sorting modules of interest include a cuvette positioned in the sample interrogation region. In embodiments, the cuvette may pass light that ranges from 100 nm to 1500 nm, such as from 150 nm to 1400 nm, such as from 200 nm to 1300 nm, such as from 250 nm to 1200 nm, such as from 300 nm to 1100 nm, such as from 350 nm to 1000 nm, such as from 400 nm to 900 nm and including from 500 nm to 800 nm.

In some embodiments, the sample interrogation region includes one or more optical adjustment components. By "optical adjustment" is meant that light irradiated onto the sample interrogation region or light collected from an irradiated flow stream is changed as desired. In some embodiments, the sample interrogation region includes an optical adjustment component for adjusting the light irradiated onto the sample interrogation region by a light source. In other embodiments, the sample interrogation region includes an optical adjustment component for adjusting light emanating from an irradiated flow stream before being conveyed to a detector for measurement. In yet other embodiments, the sample interrogation region includes an optical adjustment component for adjusting both the light irradiated onto the sample interrogation region by a light source and the light emanating from an irradiated flow stream before being conveyed to a detector for measurement. For example, the optical adjustment may be to increase the dimensions of the light, the focus of the light or to collimate the light. In some instances, optical adjustment is a magnification protocol so as to increase the dimensions of the light (e.g., beam spot), such as increasing the dimensions by 5% or more, such as by 10% or more, such as by 25% or more, such as by 50% or more and including increasing the dimensions by 75% or more. In other embodiments, optical adjustment includes focusing the collected the light so as to reduce the light dimensions, such as by 5% or greater, such as by 10% or greater, such as by 25% or greater, such as by 50% or greater and including reducing the dimensions of the beam spot by 75% or greater. In certain embodiments, optical adjustment includes collimating the light. The term "collimate" is used in its conventional sense to refer to the optically adjusting the collinearity of light propagation or reducing divergence by the light of from a common axis of propagation. In some instances, collimating includes narrowing the spatial cross section of a light beam.

Optical adjustment components may be any convenient device or structure which provides the desired change in the collected light and may include, but is not limited to, lenses, mirrors, pinholes, slits, gratings, light refractors, and any combinations thereof. The particle sorting module may include one or more optical adjustment components at the sample interrogation region as needed, such as two or more, such as three or more, such as four or more and including five or more optical adjustment components.

In some embodiments, the optical adjustment component is a focusing lens having a magnification ratio of from 0.1 to 0.95, such as a magnification ratio of from 0.2 to 0.9, such as a magnification ratio of from 0.3 to 0.85, such as a magnification ratio of from 0.35 to 0.8, such as a magnification ratio of from 0.5 to 0.75 and including a magnification ratio of from 0.55 to 0.7, for example a magnification ratio of 0.6. For example, the focusing lens is, in certain instances, a double achromatic de-magnifying lens having a magnification ratio of about 0.6. The focal length of the focusing lens may vary, ranging from 5 mm to 20 mm, such as from 6 mm to 19 mm, such as from 7 mm to 18 mm, such as from 8 mm to 17 mm, such as from 9 mm to 16 and including a focal length ranging from 10 mm to 15 mm. In certain embodiments, the focusing lens has a focal length of about 13 mm.

In other embodiments, the optical adjustment component is a collimator. The collimator may be any convenient collimating protocol, such as one or more mirrors or curved lenses or a combination thereof. For example, the collimator is in certain instances a single collimating lens. In other instances, the collimator is a collimating mirror. In yet other instances, the collimator includes two lenses. In still other instances, the collimator includes a mirror and a lens. Where the collimator includes one or more lenses, the focal length of the collimating lens may vary, ranging from 5 mm to 40 mm, such as from 6 mm to 37.5 mm, such as from 7 mm to 35 mm, such as from 8 mm to 32.5 mm, such as from 9 mm to 30 mm, such as from 10 mm to 27.5 mm, such as from 12.5 mm to 25 mm and including a focal length ranging from 15 mm to 20 mm.

In certain embodiments, the optical adjustment component is a wavelength separator. The term "wavelength separator" is used herein in its conventional sense to refer to an optical protocol for separating polychromatic light into its component wavelengths. Wavelength separation, according to certain embodiments, may include selectively passing or blocking specific wavelengths or wavelength ranges of the polychromatic light. Wavelength separation protocols of interest which may be a part of or combined with the subject flow cell nozzles, include but are not limited to, colored glass, bandpass filters, interference filters, dichroic mirrors, diffraction gratings, monochromators and combinations thereof, among other wavelength separating protocols. In some embodiments, the wavelength separator is an optical filter. For example, the optical filter may be a bandpass filter having minimum bandwidths ranging from 2 nm to 100 nm, such as from 3 nm to 95 nm, such as from 5 nm to 95 nm, such as from 10 nm to 90 nm, such as from 12 nm to 85 nm, such as from 15 nm to 80 nm and including bandpass filters having minimum bandwidths ranging from 20 nm to 50 nm.

Particle sorting modules may also include one or more containers for collecting deflected particles from the flow stream. For example, particle sorting modules may include 2 or more containers, such as 3 or more containers, such as 4 or more containers, such as 5 or more containers, such as 6 or more containers, such as 10 or more containers and including 25 or more containers. Depending on the droplet deflector, the collection containers may be spaced apart from the longitudinal axis of the flow stream by 0.001 mm or more, 0.005 mm or more, such as 0.01 mm or more, such as 0.05 mm or more, such as 0.1 mm or more, such as 0.5 mm or more, such as 1 mm or more, such as 2 mm or more, such as 5 mm or more, such as 10 mm or more, such as 15 mm or more, such as 20 mm or more, such as 25 mm or more, such as 30 mm or more, such as 35 mm or more and including 50 mm or more. For example, the collection containers may be spaced apart from the longitudinal axis of the flow stream by a distance of from 0.001 mm to 100 mm, such as from 0.005 mm to 95 mm, such as from 0.001 mm to 90 mm, such as from 0.05 mm to 85 mm, such as from 0.01 mm to 80 mm, such as from 0.05 mm to 75 mm, such as from 0.1 mm to 70 mm, such as from 0.5 mm to 65 mm, such as from 1 mm 60 mm, such as from 5 mm to 55 mm and including from 10 mm to 50 mm.

Particle Sorting Systems

Aspects of the present disclosure also include systems for sorting particle components of a sample, such as cells in a biological sample. Systems according to certain embodiments include a light source, a flow cell nozzle for flowing a flow stream, a detector for measuring one or more wavelengths of light and one or more of the subject droplet deflectors described herein that are configured to apply a deflection force at a plurality of different angles to the flow stream flowing therebetween.

In embodiments, systems include one or more light sources for irradiating the flow stream with light in one or more interrogation fields. By "interrogation field" is meant the region of the flow stream which is irradiated by the one or more light sources. Interrogation fields may vary depending on the properties of the flow stream being interrogated. In embodiments, the interrogation field may span 0.001 mm or more of the flow stream, such as 0.005 mm or more, such as 0.01 mm or more, such as 0.05 mm or more, such as 0.1 mm or more, such as 0.5 mm or more and including 1 mm or more of the flow stream. For example, the interrogation field may be a planar cross-section of the flow stream irradiated, such as, with a focused laser. In another example, the detection field may be a predetermined length of the flow stream, such as for example corresponding to the irradiation profile of a diffuse laser beam or lamp.

In some embodiments, systems of interest are configured to irradiate the flow stream at or near the break-off point of the flow stream. The term "break-off point" is used herein in its conventional sense to refer to the point in the flow stream at which the continuous flow stream begins to form droplets. For example the interrogation field may be positioned about 0.001 mm or more from the break-off point of the flow stream, such as 0.005 mm or more, such as 0.01 mm or more, such as 0.05 mm or more, such as 0.1 mm or more, such as 0.5 mm or more and including 1 mm or more from the break-off point of the flow stream. In other words, the flow stream is irradiated at a region that is 0.001 mm or more from break-off point, such as 0.005 mm or more, such as 0.01 mm or more, such as 0.05 mm or more, such as 0.1 mm or more, such as 0.5 mm or more and including irradiating the flow stream at a region which is positioned 1 mm or more of from the break-off point.

Systems include one or more light sources for irradiating the flow stream with light in one or more interrogation fields. In some embodiments, the light source is a broadband light source, emitting light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 200 nm to 1500 nm. Another example of a suitable broadband light source includes a light source that emits light having wavelengths from 400 nm to 1000 nm. Any convenient broadband light source protocol may be employed, such as a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof.

In other embodiments, the light source is a narrow band light source emitting a particular wavelength or a narrow range of wavelengths. In some instances, the narrow band light sources emit light having a narrow range of wavelengths, such as for example, 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Any convenient narrow band light source protocol may be employed, such as a narrow wavelength LED, laser diode or a broadband light source coupled to one or more optical bandpass filters, diffraction gratings, monochromators or any combination thereof.

In certain embodiments, the light source is a laser. In some instances, the subject systems include a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In others instances, the subject systems include a dye laser, such as a stilbene, coumarin or rhodamine laser. In yet other instances, lasers of interest include a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, the subject systems include a solid-state laser, such as a ruby laser, an Nd:YAG laser, NdCrYAG laser, Er:YAG laser, Nd:YLF laser, Nd:YVO$_4$ laser, Nd:YCa$_4$O(BO$_3$)$_3$ laser, Nd:YCOB laser, titanium sapphire laser, thulim YAG laser, ytterbium YAG laser, ytterbium$_2$O$_3$ laser or cerium doped lasers and combinations thereof.

The subject systems may include one or more light sources, as desired, such as two or more light sources, such as three or more light sources, such as four or more light sources, such as five or more light sources and including ten or more light sources. The light source may include any combination of types of light sources. For example, in some embodiments, the subject systems include an array of lasers, such as an array having one or more gas lasers, one or more dye lasers and one or more solid-state lasers. In other instances, where two lights sources are employed, a first light source may be a broadband white light source (e.g., broadband white light LED) and second light source may be a broadband near-infrared light source (e.g., broadband near-IR LED). In other instances, where two light sources are employed, a first light source may be a broadband white light source (e.g., broadband white light LED) and the second light source may be a narrow spectra light source (e.g., near-IR LED or laser). In yet other instances, the light source is a plurality of narrow band light sources each emitting specific wavelengths, such as two or more lasers, such as three or more lasers including 5 or more lasers. In still other instances, the light source is an array of two or more LEDs, such as an array of three or more LEDs, such as an array of five or more LEDs, including an array of ten or more LEDs.

In some embodiments, light sources emit light having wavelengths ranging from 200 nm to 1500 nm, such as from 250 nm to 1250 nm, such as from 300 nm to 1000 nm, such as from 350 nm to 900 nm and including from 400 nm to 800 nm. For example, the light source may include a broadband light source emitting light having wavelengths from 200 nm to 900 nm. In other instances, the light source includes a plurality of narrow band light sources emitting wavelengths ranging from 200 nm to 900 nm. For example, the light source may be plurality of narrow band LEDs (1 nm-25 nm) each independently emitting light having a range of wavelengths between 200 nm to 900 nm. In some embodiments, the narrow band light source is one or more narrow band lamps emitting light in the range of 200 nm to 900 nm, such as a narrow band cadmium lamp, cesium lamp, helium lamp, mercury lamp, mercury-cadmium lamp, potassium lamp, sodium lamp, neon lamp, zinc lamp or any combination thereof. In other embodiments, the narrow band light source includes one or more lasers emitting light in the range of 200 nm to 1000 nm, such as gas lasers, excimer lasers, dye lasers, metal vapor lasers and solid-state laser as described above.

Depending on the assay protocol, the subject systems may be configured to irradiate the flow stream in continuous or in discrete intervals. For example, in some embodiments, systems may be configured to irradiate the flow stream continuously. Where the light includes two or more light sources, the flow stream may be continuously irradiated by all of the light sources simultaneously. In other instances, the flow stream is continuously irradiated with each light source sequentially. In other embodiments, the flow stream may be irradiated in regular intervals, such as irradiated the sample every 0.001 microseconds, every 0.01 microseconds, every 0.1 microseconds, every 1 microsecond, every 10 microseconds, every 100 microseconds and including every 1000 microseconds.

The flow stream may be irradiated with the light source one or more times at any given measurement period, such as 2 or more times, such as 3 or more times, including 5 or more times at each measurement period.

Where more than one light source is employed, the flow stream may be irradiated at the interrogation field with the light sources simultaneously or sequentially, or a combination thereof. For example, where the flow stream is irradiated with two lasers, the subject systems may be configured to simultaneously irradiate the flow stream with both lasers. In other embodiments, the flow stream at the interrogation field is sequentially irradiated by two lasers. Where the sample is sequentially irradiated with two or more lasers, the time each light source irradiates the flow stream may independently be 0.001 microseconds or more, such as 0.01 microseconds or more, such as 0.1 microseconds or more, such as 1 microsecond or more, such as 5 microseconds or more, such as 10 microseconds or more, such as 30 microseconds or more and including 60 microseconds or more. For example, the laser may be configured to irradiate the flow stream for a duration which ranges from 0.001 microseconds to 100 microseconds, such as from 0.01 microseconds to 75 microseconds, such as from 0.1 microseconds to 50 microseconds, such as from 1 microsecond to 25 microseconds and including from 5 microseconds to 10 microseconds. In embodiments where the flow stream is sequentially irradiated by two or more lasers, the duration the flow stream is irradiated by each light source may be the same or different.

The time period between irradiation of the flow stream at the interrogation field by each light source may also vary, as desired, being separated independently by a delay of 0.001 microseconds or more, such as 0.01 microseconds or more, such as 0.1 microseconds or more, such as 1 microsecond or more, such as 5 microseconds or more, such as by 10 microseconds or more, such as by 15 microseconds or more, such as by 30 microseconds or more and including by 60 microseconds or more. For example, the time period between irradiation of the flow stream at the interrogation field by each light source may range from 0.001 microseconds to 60 microseconds, such as from 0.01 microseconds to 50 microseconds, such as from 0.1 microseconds to 35 microseconds, such as from 1 microsecond to 25 microseconds and including from 5 microseconds to 10 microseconds. In certain embodiments, the time period between irradiation of the flow stream at the interrogation field by each light source is 10 microseconds. In embodiments where the subject systems are configured to sequentially irradiate the flow stream by more than two (i.e., three or more) light sources, the delay between irradiation by each light source may be the same or different.

The light source may be positioned at a distance from the flow stream which varies depending on the type of light source and characteristics of the flow stream (e.g., flow stream width). For example, the light source may be positioned 0.01 mm or more from the flow stream, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more from the flow stream. The light source may also be positioned at an angle with respect to the flow stream in each interrogation field which also varies. For example, the light source may be positioned at an angle with respect to the axis of the flow stream which ranges from 10° to 90°, such as from 15° to 85°, such as from 20° to 80°, such as from 25° to 75° and including from 30° to 60°. In certain embodiments, the light source is positioned at a 90° angle with respect to the axis of the flow stream.

Systems of the present disclosure also include one or more detectors. Detectors of interest may include, but are not limited to optical sensors or photodetectors, such as active-pixel sensors (APSs), avalanche photodiode, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, the transmitted light is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In some embodiments, the imaging sensor is a CCD camera. For example, the camera may be an electron multiplying CCD (EMCCD) camera or an intensified CCD (ICCD) camera. In other embodiments, the imaging sensor is a CMOS-type camera. Where the transmitted light is measured with a CCD, the active detecting surface area of the CCD may vary, such as from 0.01 $cm^2$ to 10 $cm^2$, such as from 0.05 $cm^2$ to 9 $cm^2$, such as from, such as from 0.1 $cm^2$ to 8 $cm^2$, such as from 0.5 $cm^2$ to 7 $cm^2$ and including from 1 $cm^2$ to 5 $cm^2$.

The number of photodetectors in the subject systems may vary, as desired. For example, the subject systems may include one photodetector or more, such as two photodetectors or more, such as three photodetectors or more, such as four photodetectors or more, such as five photodetectors or more and including ten photodetectors or more. In certain embodiments, systems include one photodetector. In other embodiments, systems include two photodetectors. Each photodetector may be oriented with respect to proximal end of the flow cell nozzle (as referenced in an X-Y plane) at an angle which varies, such as at an angle of 60° or less, such as 55° or less, such as 50° or less, such as 45° or less, such as 30° or less, such as 15° or less, such as 10° or less and including orienting the photodetector such that the active detection surface faces the proximal end of the flow cell nozzle (FIGS. 3a and 3b)

Where the subject systems include more than one photodetector, each photodetector may be the same, or the collection of two or more photodetectors may be a combination of different photodetectors. For example, where the subject systems include two photodetectors, in some embodiments the first photodetector is a CCD-type device and the second photodetector (or imaging sensor) is a CMOS-type device. In other embodiments, both the first and second photodetectors are CCD-type devices. In yet other embodiments, both the first and second photodetectors are CMOS-type devices. In still other embodiments, the first photodetector is a CCD-type device and the second photodetector is a photomultiplier tube. In still other embodiments, the first photodetector is a CMOS-type device and the second photodetector is a photomultiplier tube. In yet other embodiments, both the first and second photodetectors are photomultiplier tubes.

In embodiments of the present disclosure, detectors of interest are configured to measure light emitted by a sample in the flow stream at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring light emitted by a sample in the flow stream at 400 or more different wavelengths.

In some embodiments, detectors of interest are configured to measure light emitted by a sample in the flow stream over a range of wavelengths (e.g., 200 nm-1000 nm). In certain embodiments, detectors of interest are configured to collect spectra of light over a range of wavelengths. For example, systems may include one or more detectors configured to collect spectra of light over one or more of the wavelength ranges of 200 nm-1000 nm. In yet other embodiments, detectors of interest are configured to measure light emitted by a sample in the flow stream at one or more specific wavelengths. For example, systems may include one or more detectors configured to measure light at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof. In certain embodiments, one or more detectors may be configured to be paired with specific fluorophores, such as those used with the sample in a fluorescence assay.

In embodiments, the detector is configured to measure light continuously or in discrete intervals. In some instances, detectors of interest are configured to take measurements of the light emitted by a sample in the flow stream continuously. In other instances, detectors of interest are configured to take measurements in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

In some instances, the photodetector also includes an optical adjustment component. In some instances, optical adjustment is a magnification protocol configured to increase the size of the field of light captured by the detector, such as by 5% or greater, such as by 10% or greater, such as by 25% or greater, such as by 50% or greater and including increasing the field of light captured by the detector by 75% or greater. In other instances, optical adjustment is a de-magnification protocol configured to decrease the field of light captured by the detector, such as by 5% or greater, such as by 10% or greater, such as by 25% or greater, such as by 50% or greater and including decreasing the field of light captured by the detector by 75% or greater. In certain embodiments, optical adjustment is a focusing protocol configured to focus the light collected by the detector, such as by focusing the beam of collected light by 5% or greater, such as by 10% or greater, such as by 25% or greater, such as by 50% or greater and including focusing the beam of collected light by 75% or greater.

Optical adjustment components may be any convenient device or structure which provides the desired change in the collected light beam and may include but is not limited to lenses, mirrors, pinholes, slits, gratings, light refractors, and any combinations thereof. The detector may include one or more optical adjustment components as needed, such as two or more, such as three or more, such as four or more and including five or more optical adjustment components. In certain embodiments, the detector includes a focusing lens. The focusing lens, for example may be a de-magnifying lens. In other instances, the focusing lens is a magnifying lens. In other embodiments, the detector includes a collimator.

In certain embodiments, systems include a combination of different optical adjustment components, such as a combination of pinholes, lenses, mirrors, slits, etc. For example, in some embodiments, systems include a focusing lens and a collimating lens. In other embodiments, systems include a collimating mirror and a focusing lens. In yet other embodiments, systems include a focusing lens and a pinhole structure. In still other embodiments, systems include a collimating lens and a pinhole structure. In still other embodiments, systems include a collimating lens and a slit structure.

In some embodiments, the detector and the optical adjustment component are in optical communication, but are not physically in contact. Depending on the size of the detector, the optical adjustment component may be positioned 0.05 mm or more from the detector, 0.1 mm or more, such as 0.5 mm or more, such as 1 mm or more, such as 10 mm or more, such as 25 mm or more, such as 50 mm or more, such as 100 mm or more, such as 250 mm or more, including 500 mm or more. In other embodiments, the optical adjustment component is physically coupled to the detector, such as with an adhesive, co-molded together or integrated together in a housing having the optical adjustment component positioned adjacent to the detector. As such, the optical adjustment component and detector may be integrated into a single unit.

In some embodiments, the optical adjustment component is a focusing lens having a magnification ratio of from 0.1 to 0.95, such as a magnification ratio of from 0.2 to 0.9, such as a magnification ratio of from 0.3 to 0.85, such as a magnification ratio of from 0.35 to 0.8, such as a magnification ratio of from 0.5 to 0.75 and including a magnification ratio of from 0.55 to 0.7, for example a magnification ratio of 0.6. For example, the focusing lens is, in certain instances, a double achromatic de-magnifying lens having a magnification ratio of about 0.6. Depending on the distance between the detector and the lens, the surface area of the detector active surface, the focal length of the focusing lens may vary, ranging from 5 mm to 20 mm, such as from 6 mm to 19 mm, such as from 7 mm to 18 mm, such as from 8 mm to 17 mm, such as from 9 mm to 16 and including a focal length ranging from 10 mm to 15 mm. In certain embodiments, the focusing lens has a focal length of about 13 mm.

In certain embodiments, optical adjustment components include one or more fiber optics which are configured to relay light from the flow cell nozzle chamber to the detector. Suitable fiber optics for propagating light from the flow cell nozzle to the active surface of the detector include, but is not limited to, flow cytometer fiber optics systems such as those described in U.S. Pat. No. 6,809,804, the disclosure of which is herein incorporated by reference.

In other embodiments, detectors of interest are coupled to a collimator. The collimator may be any convenient collimating protocol, such as one or more mirrors or curved lenses or a combination thereof. For example, the collimator is, in certain instances, a single collimating lens. In other instances, the collimator is a collimating mirror. In yet other instances, the collimator includes a series of two or more lenses, such as three or more lenses and including four or more lenses. In still other instances, the collimator includes a mirror and a lens. Where the collimator includes one or more lenses, the focal length of the collimating lens may vary, ranging from 5 mm to 40 mm, such as from 6 mm to 37.5 mm, such as from 7 mm to 35 mm, such as from 8 mm to 32.5 mm, such as from 9 mm to 30 mm, such as from 10 mm to 27.5 mm, such as from 12.5 mm to 25 mm and including a focal length ranging from 15 mm to 20 mm.

In certain embodiments, the optical adjustment component is a wavelength separator. As discussed above, wavelength separators of interest refer to an optical protocol for separating polychromatic light into its component wavelengths for detection. Wavelength separation, according to certain embodiments, may include selectively passing or blocking specific wavelengths or wavelength ranges of the polychromatic light. To separate wavelengths of light, the light emitted by a sample in the flow stream may be passed through any convenient wavelength separating protocol, including but not limited to colored glass, bandpass filters, interference filters, dichroic mirrors, diffraction gratings, monochromators and combinations thereof, among other wavelength separating protocols. Systems may include one or more wavelength separators, such as two or more, such as three or more, such as four or more, such as five or more and including 10 or more wavelength separators. In one example, detectors include one bandpass filter. In another example, detectors include two or more bandpass filters. In another example, detectors include two or more bandpass filters and a diffraction grating. In yet another example, detectors include a monochromator. In certain embodiments, detectors include a plurality of bandpass filters and diffraction gratings configured into a filter wheel setup. Where detectors include two or more wavelength separators, the wavelength separators may be utilized individually or in series to separate polychromatic light into component wavelengths. In some embodiments, wavelength separators are arranged in series. In other embodiments, wavelength separators are arranged individually such that one or more measurements are conducted using each of the wavelength separators.

In some embodiments, detectors include one or more optical filters, such as one or more bandpass filters. For example, optical filters of interest may include bandpass filters having minimum bandwidths ranging from 2 nm to 100 nm, such as from 3 nm to 95 nm, such as from 5 nm to 95 nm, such as from 10 nm to 90 nm, such as from 12 nm to 85 nm, such as from 15 nm to 80 nm and including bandpass filters having minimum bandwidths ranging from 20 nm to 50 nm. In other embodiments, the wavelength separator is a diffraction grating. Diffraction gratings may include, but are not limited to transmission, dispersive or reflective diffraction gratings. Suitable spacings of the diffraction grating may vary depending on the configuration of the flow nozzle chamber, detector and other optical adjust protocols present (e.g., focusing lens), ranging from 0.01 µm to 10 µm, such as from 0.025 µm to 7.5 µm, such as from 0.5 µm to 5 µm, such as from 0.75 µm to 4 µm, such as from 1 µm to 3.5 µm and including from 1.5 µm to 3.5 µm.

In certain embodiments, the subject systems are flow cytometric systems employing the above described droplet deflectors for applying a deflection force to droplets in a flow stream to sort particles in a sample. For example the flow cytometer may include one or more of the above-described droplet deflectors that are configured to apply a deflection force at a plurality of different angles to target droplets in a flow stream flowing therebetween. Suitable flow cytometry systems and methods for analyzing samples include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem. January;* 49(pt 1):17-28; Linden, et. al., *Semin Throm Hemost.* 2004 October; 30(5):502-11; Alison, et al. *J Pathol,* 2010 December; 222(4):335-344; and Herbig, et al. (2007) *Crit Rev Ther Drug Carrier Syst.* 24(3):203-255; the disclosures of which are incorporated herein by reference. In certain instances, flow cytometry systems of interest include BD Biosciences FACSCanto™ flow cytometer, BD Biosciences FACSVantage™, BD Biosciences FACSort™, BD Biosciences FACSCount™, BD Biosciences FACScan™, and BD Biosciences FACSCalibur™ systems, a BD Biosciences Influx™ cell sorter, BD Biosciences Jazz™ cell sorter and BD Biosciences Aria™ cell sorter or the like.

In certain embodiments, the subject systems are flow cytometer systems which incorporate one or more components of the flow cytometers described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494 and 9,097,640; the disclosures of which are herein incorporated by reference.

Methods for Sorting Particle Components of a Sample in a Flow Stream

Aspects of the disclosure also include methods for sorting particles of a sample, such as cells in a biological sample. Methods according to certain embodiments include irradiating a sample containing particles in a flow stream in an interrogation region of a particle sorting module, detecting light (e.g., fluorescent light) from the sample, and sorting the particles of the sample into two or more sample collection containers. In certain embodiments, the sample is a biological sample and methods include sorting and collecting two or more different types of cells.

In some embodiments, the sample is a biological sample. The term "biological sample" is used in its conventional sense to refer to a whole organism, plant, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may be any type of organismic tissue, including both healthy and diseased tissue (e.g., cancerous, malignant, necrotic, etc.). In certain embodiments, the biological sample is a liquid sample, such as blood or derivative thereof, e.g., plasma, tears, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.).

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

Cells of interest may be targeted for separation from the flow stream according to a variety of parameters, such as a phenotypic characteristic identified via the attachment of a particular fluorescent label to cells of interest. In some embodiments, the system is configured to deflect analyzed droplets that are determined to include a target cell. A variety of cells may be targeted for sorting using the subject methods. Target cells of interest include, but are not limited to, stem cells, T cells, dendritic cells, B Cells, granulocytes, leukemia cells, lymphoma cells, virus cells (e.g., HIV cells) NK cells, macrophages, monocytes, fibroblasts, epithelial cells, endothelial cells, and erythroid cells. Target cells of interest include cells that have a convenient cell surface marker or antigen that may be captured or labelled by a convenient affinity agent or conjugate thereof. For example, the target cell may include a cell surface antigen such as CD11b, CD123, CD14, CD15, CD16, CD19, CD193, CD2, CD25, CD27, CD3, CD335, CD36, CD4, CD43, CD45RO, CD56, CD61, CD7, CD8, CD34, CD1c, CD23, CD304, CD235a, T cell receptor alpha/beta, T cell receptor gamma/delta, CD253, CD95, CD20, CD105, CD117, CD120b, Notch4, Lgr5 (N-Terminal), SSEA-3, TRA-1-60 Antigen, Disialoganglioside GD2 and CD71. In some embodiments, the target cell is selected from HIV containing cell, a Treg cell, an antigen-specific T-cell populations, tumor cells or hematopoetic progenitor cells (CD34+) from whole blood, bone marrow or cord blood.

In practicing the subject methods, a fluidic sample including target particles is first introduced into the particle sorting module flow nozzle. Upon exit from the flow nozzle, the particles are passed substantially one at a time through the sample interrogation where each of the particles is irradiated to a source of light and measurements of light scatter parameters and fluorescent emissions as desired (e.g., two or more light scatter parameters and measurements of one or more fluorescent emissions) are separately recorded for each particle. The particles are passed in the flow stream substantially one at a time in a flow path through the sample interrogation region in the particle sorting module where each particle is illuminated by a light source. Depending on the properties of the flow stream being interrogated, 0.001 mm or more of the flow stream may be irradiated with light, such as 0.005 mm or more, such as 0.01 mm or more, such as 0.05 mm or more, such as 0.1 mm or more, such as 0.5 mm or more and including 1 mm or more of the flow stream may be irradiated with light. In certain embodiments, methods include irradiating a planar cross-section of the flow stream in the sample interrogation region, such as with a laser (as described above). In other embodiments, methods include irradiating a predetermined length of the flow stream in the sample interrogation region, such as corresponding to the irradiation profile of a diffuse laser beam or lamp.

In certain embodiments, methods including irradiating the flow stream at or near the flow cell nozzle orifice. For example, methods may include irradiating the flow stream at a position about 0.001 mm or more from the nozzle orifice, such as 0.005 mm or more, such as 0.01 mm or more, such as 0.05 mm or more, such as 0.1 mm or more, such as 0.5 mm or more and including 1 mm or more from the nozzle orifice. In certain embodiments, methods include irradiating the flow stream immediately adjacent to the flow cell nozzle orifice.

In series with a sensing region, detectors, such as photomultiplier tubes (or "PMT"), are used to record light that passes through each particle (in certain cases referred to as forward light scatter), light that is reflected orthogonal to the direction of the flow of the particles through the sensing region (in some cases referred to as orthogonal or side light scatter) and fluorescent light emitted from the particles, if it is labeled with fluorescent marker(s), as the particle passes through the sensing region and is illuminated by the energy source. Each of forward light scatter (or FSC), orthogonal light scatter (SSC), and fluorescence emissions (FL1, FL2, etc.) include a separate parameter for each particle (or each "event"). Thus, for example, two, three or four parameters can be collected (and recorded) from a particle labeled with two different fluorescence markers.

As described above, suitable light detecting protocols, include but are not limited to optical sensors or photodetectors, such as active-pixel sensors (APSs), avalanche photodiode, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, light from the irradiated flow stream at the sample interrogation region of the particle sorting module is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In certain embodiments, light is measured with a charge-coupled device (CCD). Where the light from the irradiated flow stream at the sample interrogation region of the particle sorting module is measured with a CCD, the active detecting surface area of the CCD may vary, such as from 0.01 $cm^2$ to 10 $cm^2$, such as from 0.05 $cm^2$ to 9 $cm^2$, such as from, such as from 0.1 $cm^2$ to 8 $cm^2$, such as from 0.5 $cm^2$ to 7 $cm^2$ and including from 1 $cm^2$ to 5 $cm^2$.

The data recorded for each particle is analyzed in real time or stored in a data storage and analysis means, such as a computer, as desired. U.S. Pat. No. 4,284,412 describes the configuration and use of a flow cytometer of interest equipped with a single light source while U.S. Pat. No. 4,727,020 describes the configuration and use of a flow cytometer equipped with two light sources.

In embodiments of the present disclosure according to certain embodiments, the particles are detected and uniquely identified by exposing the particles to excitation light and measuring the fluorescence of each particle in one or more detection channels, as desired. Fluorescence emitted in detection channels used to identify the particles and binding complexes associated therewith may be measured following excitation with a single light source, or may be measured separately following excitation with distinct light sources. If separate excitation light sources are used to excite the particle labels, the labels may be selected such that all the labels are excitable by each of the excitation light sources used.

Methods in certain embodiment also include data acquisition, analysis and recording, such as with a computer, wherein multiple data channels record data from each detector for the light scatter and fluorescence emitted by each particle as it passes through the sample interrogation region of the particle sorting module. In these embodiments, analysis includes classifying and counting particles such that each particle is present as a set of digitized parameter values. The subject systems may be set to trigger on a selected parameter in order to distinguish the particles of interest from background and noise. "Trigger" refers to a preset threshold for detection of a parameter and may be used as a means for detecting passage of a particle through the light source. Detection of an event that exceeds the threshold for the selected parameter triggers acquisition of light scatter and fluorescence data for the particle. Data is not acquired for particles or other components in the medium being assayed which cause a response below the threshold. The trigger parameter may be the detection of forward scattered light caused by passage of a particle through the light beam. The flow cytometer then detects and collects the light scatter and fluorescence data for the particle.

A particular subpopulation of interest is then further analyzed by "gating" based on the data collected for the entire population. To select an appropriate gate, the data is plotted so as to obtain the best separation of subpopulations possible. This procedure may be performed by plotting forward light scatter (FSC) vs. side (i.e., orthogonal) light scatter (SSC) on a two dimensional dot plot. A subpopulation of particles is then selected (i.e., those cells within the gate) and particles that are not within the gate are excluded. Where desired, the gate may be selected by drawing a line around the desired subpopulation using a cursor on a computer screen. Only those particles within the gate are then further analyzed by plotting the other parameters for these particles, such as fluorescence. Where desired, the above analysis may be configured to yield counts of the particles of interest in the sample.

To sort the target droplets containing particles of interest, the analyzed flow stream is subjected to a deflection force by a droplet deflector (as described above). A voltage is applied to each set of parallel metallic plates and droplets flowing therethrough are accelerated and deflected at a plurality of different angles based on the charge and polarity of the charge of the droplet. The voltage applied to deflector plates to divert charged particles may be 10 mV or more, such as 25 mV or more, such as 50 mV or more, such as 100 mV or more, such as 250 mV or more, such as 500 mV or more, such as 750 mV or more, such as 1000 mV or more, such as 2500 mV or more, such as 5000 mV or more, such as 10000 V or more, such as 15000 V or more, such as 25000 V or more, such as 50000 V or more and including 100000 V or more. In certain embodiments, the voltage applied to each set of parallel metallic plates is from 0.5 kV to 15 kV, such as from 1 kV to 15 kV, such as from 1.5 kV to 12.5 kV and including from 2 kV to 10 kV. As such, the electric field strength between the metallic plates ranges from 0.1 V/m to $1 \times 10^7$ V/m, such as from 0.5 V/m to $5 \times 10^6$, such as from 1 V/m to $1 \times 10^6$ V/m, such as from 5 V/m to $5 \times 10^5$ V/m, such as from 10 V/m to $1 \times 10^5$ V/m and including from 50 V/m to $5 \times 10^4$ V/m, for example $1 \times 10^5$ V/m to $2 \times 10^6$ V/m.

Where the droplet deflector includes two or more sets of parallel metallic plates, the voltage applied to each set of parallel of metallic plates may be different, where the voltage applied to each set of parallel metallic plates may differ by 0.01 mV or more, such as 0.05 mV or more, such as 0.1 mV or more, such as 0.5 mV or more, such as 1 mV or more, such as 5 mV or more, such as 10 mV or more, such as 25 mV or more, such as 50 mV or more, such as 75 mV or more, such as 100 mV or more, such as 250 mV or more, such as 500 mV or more, such as 750 mV or more, such as 1 V or more, such as 2.5 V or more, such as 5 V or more, such as 10 V or more, such as 25 V or more, such as 50 V or more and including 100 V or more. As such, the electric field strength between each set of parallel metallic plate may differ by 0.001 V/m or more, such as 0.01 V/m or more, such as 0.1 V/m or more, such as 0.5 V/m or more, such as 1 V/m or more, such as 2 V/m or more, such as 5 V/m or more, such as 10 V/m or more and including 25 V/m or more.

In certain embodiments, the system operates to determine a timeslot during which one or more sample collection containers are aligned with the deflected droplet receiving location. In some instances, the deflection signal includes an initial deflection sub-signal and a final deflection sub-signal; and the system operates to produce the deflection signal by sending an initial deflection sub-signal at the beginning of the timeslot that configures the deflector to deflect an analyzed droplet, when present. In certain cases, methods include sending a final deflection sub-signal at the end of the timeslot that configures the droplet deflector not to deflect an analyzed droplet. In some embodiments, methods include sending a final deflection sub-signal after a single analyzed droplet has been deflected during the timeslot, where the final deflection sub-signal configures the droplet deflector not to deflect an analyzed droplet.

Computer-Controlled Systems

Aspects of the present disclosure further include computer controlled systems for practicing the subject methods, where the systems further include one or more computers for complete automation or partial automation of a system for practicing methods described herein. In some embodiments, systems include a computer having a computer readable storage medium with a computer program stored thereon, where the computer program when loaded on the computer includes instructions for irradiating a sample in a flow stream in the sample interrogation region; algorithm for detecting light from the sample and measuring the detected light at one or more wavelengths and algorithm for sorting particles in the sample by deflecting droplets of the flow stream at a plurality of different angles into two or more sample collection containers.

In embodiments, the system includes an input module, a processing module and an output module. In some embodiments, the subject systems may include an input module such that parameters or information about each fluidic sample, intensity and wavelengths (discrete or ranges) of the applied light source, properties of the particle sorting module including flow cell nozzle chamber size, nozzle orifice size, dimensions of sample interrogation region of the particle sorting module, the applied voltage of each set of deflection plates, position of containers at the distal end of the particle sorting module, duration of irradiation by the light source, number of different light sources, distance from light source to the flow stream in the sample interrogation region of the particle sorting module, focal length of any optical adjustment components, refractive index of flow stream medium (e.g., sheath fluid), presence of any wavelength separators, properties of wavelength separators including bandpass width, opacity, grating spacting as well as properties and sensitivity of photodetectors.

The processing module includes memory having a plurality of instructions for performing the steps of the subject methods, such as irradiating a sample in a flow stream in the sample interrogation region of a particle sorting module; detecting light from the sample in the flow stream, measuring the detected light at one or more wavelengths and sorting particles in the sample into two or more sample collection containers.

After the processing module has performed one or more of the steps of the subject methods, an output module communicates the results to the user, such as by displaying on a monitor or by printing a report.

The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

Systems may include a display and operator input device. Operator input devices may, for example, be a keyboard, mouse, or the like. The processing module includes a processor which has access to a memory having instructions stored thereon for performing the steps of the subject methods, such as irradiating a sample in a flow stream in the sample interrogation region of a particle sorting module; detecting light from the sample in the flow stream, measuring the detected light at one or more wavelengths and sorting particles in the sample into two or more sample collection containers.

The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a computer connected to a Wide Area Network ("WAN"), telephone network, satellite network, or any other suitable communication channel, including a mobile telephone (i.e., smartphone).

In some embodiments, systems according to the present disclosure may be configured to include a communication interface. In some embodiments, the communication interface includes a receiver and/or transmitter for communicating with a network and/or another device. The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, an RS-232 port, or any other suitable electrical connection port to allow data communication between the subject systems and other external devices such as a computer terminal (for example, at a physician's office or in hospital environment) that is configured for similar complementary data communication.

In one embodiment, the communication interface is configured for infrared communication, Bluetooth® communication, or any other suitable wireless communication protocol to enable the subject systems to communicate with other devices such as computer terminals and/or networks, communication enabled mobile telephones, personal digital assistants, or any other communication devices which the user may use in conjunction therewith, in managing the treatment of a health condition, such as HIV, AIDS or anemia.

In one embodiment, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In one embodiment, the subject systems are configured to wirelessly communicate with a server device via the communication interface, e.g., using a common standard such as 802.11 or Bluetooth® RF protocol, or an IrDA infrared protocol. The server device may be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen.

In some embodiments, the communication interface is configured to automatically or semi-automatically communicate data stored in the subject systems, e.g., in an optional data storage unit, with a network or server device using one or more of the communication protocols and/or mechanisms described above.

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Windows XP, Windows 7, Windows 8, iOS, Sun Solaris, Linux, OS/400, Compaq Tru64 Unix, SGI IRIX, Siemens Reliant Unix, and others.

Kits

Aspects of the invention further include kits, where kits include one or more of the droplet deflectors as described herein. In some embodiments, kits include the one or more sets of parallel metallic plates of the subject droplet deflectors along with instructions for assembling each set of parallel metallic plates. In certain instances, kits can include one or more assay components (e.g., labeled reagents, buffers, etc., such as described above). In some instances, the kits may further include a sample collection device, e.g., a lance or needle configured to prick skin to obtain a whole blood sample, a pipette, etc., as desired.

The various assay components of the kits may be present in separate containers, or some or all of them may be pre-combined. For example, in some instances, one or more components of the kit, e.g., each set of parallel metallic plates are present in a sealed pouch, e.g., a sterile foil pouch or envelope.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

Utility

The subject droplet deflectors, particle sorting modules, particle sorting systems, methods and computer systems find use in a variety of applications where it is desirable to analyze and sort particle components in a sample in a fluid medium, such as a biological sample. Embodiments of the invention find use where it is desirable to provide a flow cytometer with improved cell sorting accuracy, enhanced particle collection, particle charging efficiency, more accurate particle charging and enhanced particle deflection during cell sorting.

Embodiments of the invention also find use in applications where cells prepared from a biological sample may be desired for research, laboratory testing or for use in therapy. In some embodiments, the subject methods and devices may facilitate obtaining individual cells prepared from a target fluidic or tissue biological sample. For example, the subject methods and systems facilitate obtaining cells from fluidic or tissue samples to be used as a research or diagnostic specimen for diseases such as cancer. Likewise, the subject methods and systems may facilitate obtaining cells from fluidic or tissue samples to be used in therapy. Methods and devices of the present disclosure allow for separating and collecting cells from a biological sample (e.g., organ, tissue, tissue fragment, fluid) with enhanced efficiency and low cost as compared to traditional flow cytometry systems.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A particle sorting module comprising:
   a flow cell nozzle comprising a nozzle orifice configured to flow a flow stream through the flow cell nozzle; and
   a droplet deflector configured to apply a deflection force from a plurality of different directions to the flow stream flowing therebetween, wherein the droplet deflector comprises two parallel twisted metallic plates.

2. The particle sorting module according to claim 1, wherein the deflection force is constant along the length of the twisted metallic plates.

3. The particle sorting module according to claim 1, wherein the metallic plates have a width from 0.5 mm to 10 mm.

4. The particle sorting module according to claim 1, wherein the metallic plates have a length from 1 mm to 25 mm.

5. The particle sorting module according to claim 1, wherein the twist angle is 5° or more.

6. The particle sorting module according to claim 5, wherein the twist angle is 30° or more.

7. The particle sorting module according to claim 1, wherein the two parallel twisted metallic plates are spaced apart by 1 mm or more.

8. A system comprising:
   a light source;
   a flow cell nozzle comprising a nozzle orifice configured to flow a flow stream through the flow cell nozzle;
   a detector for measuring one or more wavelengths of light; and
   a droplet deflector configured to apply a deflection force from a plurality of different directions to the flow stream flowing therebetween, wherein the droplet deflector comprises two parallel twisted metallic plates.

9. The system according to claim 8, wherein the deflection force is constant along the length of the twisted metallic plates.

10. The system according to claim 8, wherein the metallic plates have a width from 0.5 mm to 10 mm.

11. The system according to claim 8, wherein the metallic plates have a length from 1 mm to 25 mm.

12. The system according to claim 8, wherein the twist angle is 5° or more.

13. The system according to claim 12, wherein the twist angle is 30° or more.

14. The system according to claim 8, wherein the two parallel twisted metallic plates are spaced apart by 1 mm or more.

15. A method comprising:
    irradiating with a light source a sample comprising particles in a flow stream;
    detecting one or more wavelengths of light; and
    sorting the particles in the sample into two or more sample collection containers with a droplet deflector configured to apply a deflection force from a plurality of different directions to the flow stream flowing therebetween, wherein the droplet deflector comprises two parallel twisted metallic plates.

16. The method according to claim 15, wherein the deflection force is constant along the length of the twisted metallic plates.

17. The method according to claim 15, wherein the metallic plates have a width from 0.5 mm to 10 mm.

18. The method according to claim 15, wherein the metallic plates have a length from 1 mm to 25 mm.

19. The method according to claim 15, wherein the twist angle is 5° or more.

20. The method according to claim 19, wherein the twist angle is 30° or more.

21. The method according to claim 15, wherein the two parallel twisted metallic plates are spaced apart by 1 mm or more.

* * * * *